(12) United States Patent
Deusser et al.

(10) Patent No.: US 8,191,729 B2
(45) Date of Patent: Jun. 5, 2012

(54) DEVICE AND METHOD FOR MIXING BONE CEMENT

(75) Inventors: Stefan Deusser, Karlstein (DE); Christoph Sattig, Dieburg (DE)

(73) Assignee: aap Biomaterials GmbH, Dieburg (DE)

( * ) Notice: Subject to any disclaimer, the term of this patent is extended or adjusted under 35 U.S.C. 154(b) by 927 days.

(21) Appl. No.: 12/200,415

(22) Filed: Aug. 28, 2008

(65) Prior Publication Data
US 2009/0080284 A1    Mar. 26, 2009

(30) Foreign Application Priority Data
Sep. 1, 2007   (DE) .................. 10 2007 041 666

(51) Int. Cl.
*B01F 15/02*   (2006.01)
(52) U.S. Cl. ....................... 220/801; 366/347
(58) Field of Classification Search ............... 92/110; 220/216, 227, 351, 801, 805; 366/347
See application file for complete search history.

(56) References Cited

U.S. PATENT DOCUMENTS

| 363,517 A | * | 5/1887 | Haigh ...................... 220/227 |
| 836,350 A | * | 11/1906 | Webb ...................... 60/547.1 |
| 2,983,256 A | * | 5/1961 | Seeloff ...................... 92/110 |
| 4,185,072 A | | 1/1980 | Frakes et al. |
| 5,462,356 A | | 10/1995 | Murray |
| 5,549,381 A | | 8/1996 | Hays et al. |

FOREIGN PATENT DOCUMENTS

EP    0178658 A2    4/1986

OTHER PUBLICATIONS

S. Josten, "EP Patent Application No. EP 08 01 3144 Search Report", Dec. 30, 2008, Publisher: EPO, Published in: EP.

* cited by examiner

*Primary Examiner* — David Sorkin
(74) *Attorney, Agent, or Firm* — DeMont & Breyer, LLC

(57) ABSTRACT

Device and method for mixing bone cement, for injection into vertebra in particular, comprising a mixing beaker (1), manual stirring rod (6) and a cover (2), which fits in said mixing beaker (1) with a perfect fit, and the lowermost point of which features an extraction hollow cone (3) in which an extraction syringe for extraction by suction of bone cement mixed in said mixing beaker (1) is provided.

13 Claims, 3 Drawing Sheets

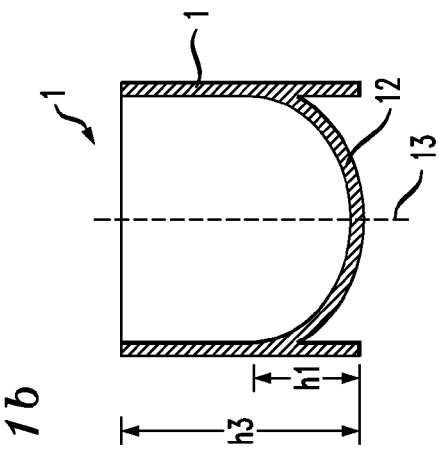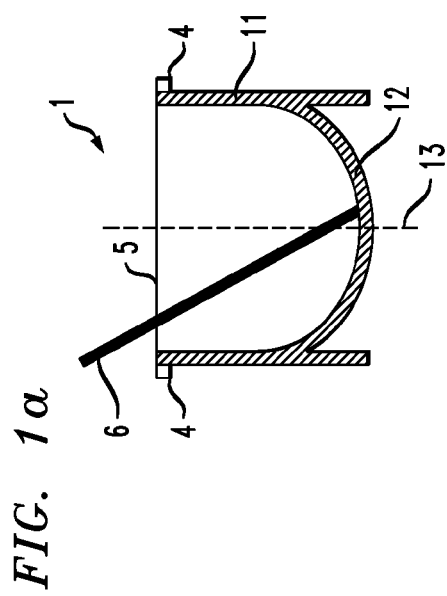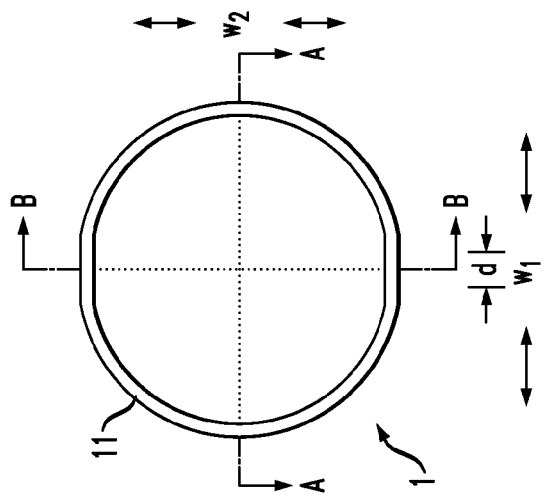

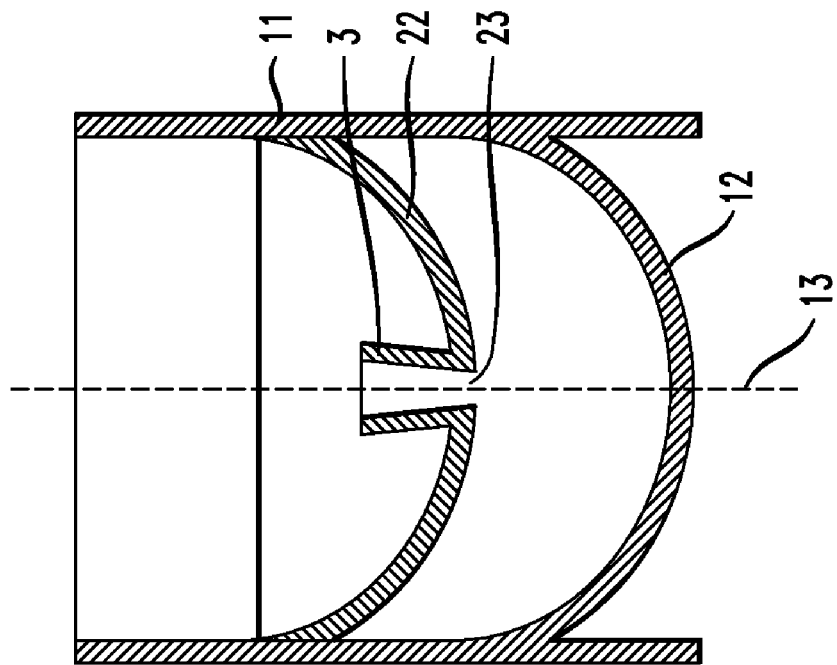
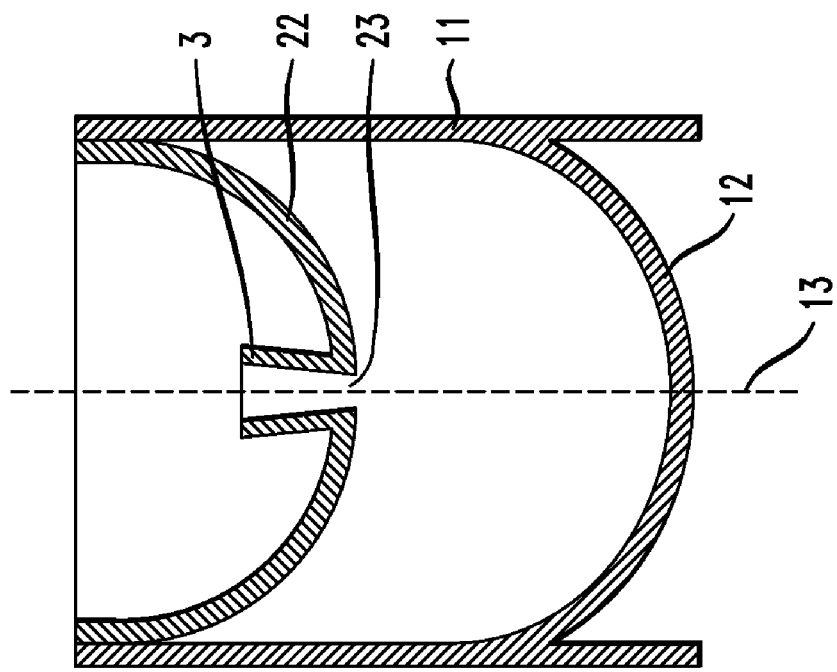

DEVICE AND METHOD FOR MIXING BONE CEMENT

FIELD OF THE INVENTION

The invention relates to a device and method for mixing pastes, a bone cement mixture in particular, for injection in vertebra.

BACKGROUND OF THE INVENTION

Within the scope of treatments for vertebroplasty and kyphoplasty, mixed pastes are employed to fill and stabilize vertebra, e.g., with recent fractures.

The bone cement required for this consists either of hydroxyl apatite, a calcium phosphate salt, or of acrylates. Both types are mixed of two components, one solid and one liquid, and set in situ.

Various devices and methods are known for mixing bone cement. Thus, EP 0 178 658 A2 describes a device and method for the manufacture of bone cement for the purpose of anchoring prosthetics, such as artificial hip joints. The device comprises a vessel in which bone cement is mixed by means of a motor-driven stirrer. The vigorous stirring leads to inclusions of air in the mixture of bone cement, which must be removed. Connected to the mixing vessel for said purpose is a suction pump, which, during the mixing process produces a vacuum inside the vessel. During extraction of the bone cement, air is prevented from reaching the extraction syringe.

The stirrer and requisite pump are cost-intensive. A further disadvantage is that the known device can only be used to mix substantial amounts of bone cement.

GENERAL DESCRIPTION OF THE INVENTION

The purpose of the invention consists in furnishing a simple and cost effective device for mixing bone cement.

A further purpose of the invention consists in furnishing mixed bone cement in a smaller quantity, as required for injection into vertebra.

Further, the underlying purpose of the invention is to prevent air from getting in the extraction device during extraction of the mixed bone cement.

In order to achieve said purposes, a mixing vessel is employed in which a small quantity of bone cement of two components can be mixed together manually with the aid of a manual stirring rod.

The interior of the plastic mixing vessel is of a non-angular shape, so that no mixture content remains in dead angles; this prevents corruption of the mixing ratio in the usable volume of the mixing beaker. In addition, only a small amount of residual bone cement can remain inside the vessel.

As soon as the bone cement is mixed, a cover is inserted in the mixing vessel. Subsequently, the cover is lowered by being pressed down in the mixing vessel. By this, air originally present between bone cement and cover is pressed out between the side walls of the vessel and cover as well as through the center opening. The cover ultimately is seated on the mixed bone cement, such that no more air whatsoever is present above the cement. After the cover has been lowered, the mixing vessel with mixed bone cement located therein therefore is closed or "sealed" in an airtight manner.

Located on the bottom end of the cover is a conical extraction device for the purpose of extracting mixed bone cement. Said extraction device is constructed in such a way that extraction is possible only by means thereof. The small cross section minimizes exposure by means of monomer vapors of surgical personnel. Said extraction device preferably involves a luer cone.

Inserted in said extraction device are one extraction syringe, or several in succession, with which the mixed bone cement can be extracted by suction from the mixing vessel. During the suction process, outer air pressure presses the cover downward in a manner corresponding to the quantity of bone cement extracted by suction, with the gap between mixing vessel and cover being kept sealed by the plastic bone cement mixture. This therefore prevents air from getting into the mixture and, thus, into the extraction syringe during the extraction process.

As soon as the desired quantity of bone cement has been extracted, the extraction syringe is removed.

In one embodiment of the invention, the mixing vessel is used as a delivery vessel for one component of the bone cement to be mixed, preferably the solid component. For this purpose, the mixing vessel is sealed by means of a cover film with the component located therein and, indeed, said cover film preferably is affixed to a flange located on the upper edge of the mixing vessel. The mixing vessel can be commercially distributed as a "set" in this form, together, e.g., with a manual stirring rod, the cover and the second component of said bone cement to be mixed at a later time.

BRIEF DESCRIPTION OF THE FIGURES

One embodiment of the invention is described with the aid of drawings.

In this connection:

FIG. 1a shows a vertical section of a mixing beaker according to the invention, corresponding to Section AA in FIG. 1c, FIG. 1b shows said mixing beaker in vertical section, corresponding to Section BB in FIG. 1c, FIG. 1c shows the mixing beaker in top view, FIG. 3a shows the cover in an inserted, not lowered state, and FIG. 3b shows a vertical section of the cover in the lowered state.

DETAILED DESCRIPTION OF THE INVENTION

Figure 2A:
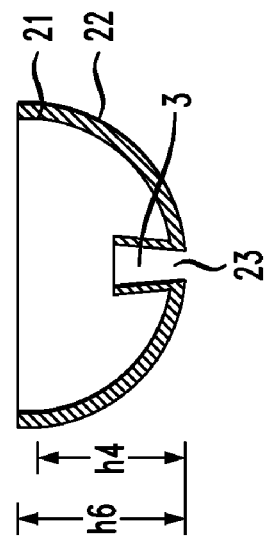
FIG. 2a shows a vertical section of a cover of said mixing beaker, corresponding to Section AA in FIG. 2c.

FIGS. 1a and 1b show a mixing beaker (1) according to the invention in, in each case, vertical section. The mixing beaker (1) has a bottom (12) of concave shape. Joined to said bottom (12) is a side wall (11) which forms feet in a downward direction and which is raised in an upward direction.

A flange (4) can run on the upper end of the side wall (11) to which flange a cover film (5) can be affixed.

The overall configuration of the mixing beaker (1) features a symmetrical axis (13). In axial section the concavity of the bottom (12) appears as an approximately half-ellipsoid. The raised side wall progresses parallel to the symmetrical axis (13).

The bottom (12) features a height (h1) of 22 mm±50%, to which is joined a side wall for a distance (h2) of 20 mm±50%, yielding an overall height (h3) of the mixing beaker of 42 mm±50%.

FIG. 1c shows the mixing beaker (1) in top view. The side wall (11) features a corner-less cross section, without being circular. In a preferred embodiment of the invention, the side wall (11) forms an approximately elliptical cylinder featuring, in the largest dimension thereof, an interior width ($w_1$) of 49 mm±50%. Perpendicular to this, the interior width ($w_2$) of the approximate ellipse is 44 mm±50%. The difference between said two values is based on the fact that in the largest dimension the side wall (11) features two opposing linear segments of 5 mm±50%.

FIG. 2a shows the cover (2) of the device according to the invention in vertical section. Located on the lowermost point of the cover (2) is an extraction hollow cone (3), which pierces the wall of the bottom (22). This extraction hollow cone (3) preferably involves a 6% luer cone according to ISO 594-1. With regard to the geometry of the extraction hollow cone (3), this signifies that the side wall of the extraction hollow cone (3) features a 6% incline.

A luer cone involves a standardized connecting system for cannulas, syringes and infusion tubes in the medical field. The seal for the invention between extraction hollow cone (3) and extraction syringe is obtained by means of a conical construction of the connecting parts.

The extraction hollow cone (3) is designed for anchorage of an extraction syringe (not illustrated), with which mixed bone cement can be extracted by suction from the mixing beaker (1).

Figure 2B:
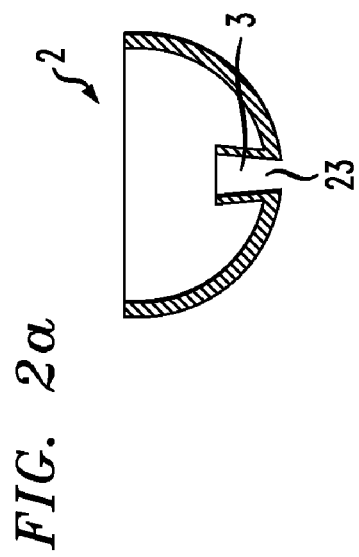
FIG. 2b shows the cover in vertical section, corresponding to Section BB in FIG. 2c.

FIG. 2b shows in vertical section the cover (2) of the device according to the invention. In every embodiment, the outside width of the side wall (21) of the cover (2) is identical to the inside width of the side wall (11) of the mixing beaker (1) in order to assure that the cover (2) fits in the mixing beaker (1) with a perfect fit.

The concave bottom (22) of the cover (2) extends up to a height (h4) of 22 mm±50% measured from the lowermost point of the cover (2). Joined to the concave bottom (22) is a raised side wall (21) having a height (h5) of 3 mm±50%, yielding a value of 25 mm±50% for the overall height (h6) of the cover (2) of the device according to the invention.

Figure 2C:
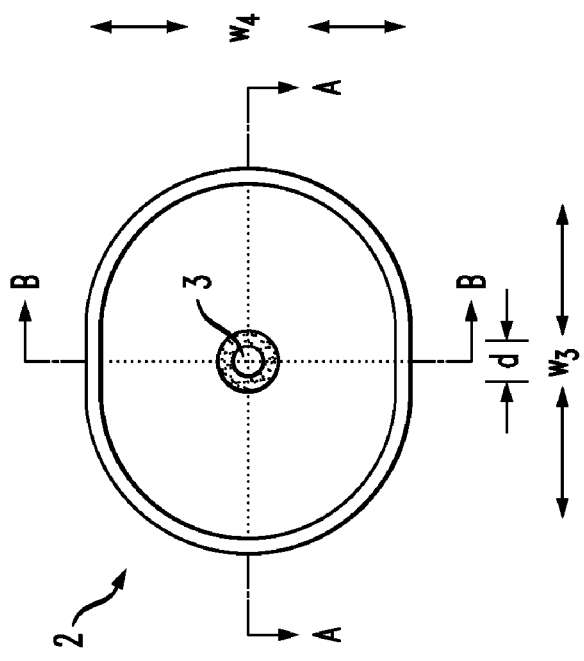
FIG. 2c shows the cover in top view.

FIG. 2c shows the dimensions of the cover of the device according to the invention in top view. The side wall (21) forms an approximate ellipse, the largest dimension of which features an outside width ($w_3$) of 49 mm±50%. Perpendicular to this, the outside width (w4) of the approximate ellipse is 44 mm±50%. The difference between said two values is based on the fact that in the largest dimension the side wall (21) features two opposing linear segments of 5 mm±50%. This design prevents a twisting of the cover when affixing and removing the extraction system.

FIG. 3a shows in vertical section the mixing beaker (1) according to the invention with inserted cover (2), with the cover (2) being located, with a perfect fit, in the upper area of the mixing beaker (1).

FIG. 3b shows in vertical section the mixing beaker (1) according to the invention with inserted cover (2), with the cover (2) having been lowered to an extent that only bone cement mixture is located in the vessel interior, i.e., lowering the cover has laterally displaced air, which initially had been located between the surface of the mixture and the cover, via the gap between vessel wall (11) and cover (2) and via the extraction opening. In this state the mixture is almost completely closed by means of the cover. Only the cross section of the center opening communicates with the ambient air.

Operation of the Mixing Device is as Follows:

A manual stirring rod (6) can be used to manually stir bone cement at the bottom of the mixing beaker (1). The bone cement is manufactured of two components, one solid, possibly powder-form, and one liquid. Since the bottom (12) features a rounded shape, components of the mixture or residues cannot accumulate at any point of the bottom (12).

After bone cement of two components has been mixed manually in the mixing beaker (1) by means of the manual stirring rod (6), the cover (2) is inserted in the mixing beaker (1) (FIG. 3a). The cover (2) inserted in this way is pressed down in the mixing beaker (1) in order to displace air, located above the mixed bone cement, out of the mixing beaker (1) laterally and through the center opening. In the next step, the port of an extraction syringe is introduced in the extraction hollow cone (3). The mixed bone cement is now extracted by suction from the mixing beaker (1) by means of the extraction syringe inserted in this way. During said extraction process, the cover (2) lowers according to the extracted quantity of mixed bone cement, since the cover (2) is seated in the mixing beaker with a perfect fit and the mixed bone cement acts as a sealing agent. Consequently, the area of the mixing beaker (1) in which the mixed bone cement is located is closed, relative to the outside world. Air pressure outside the mixing vessel (1) with inserted cover (2) therefore causes the cover (2) to lower during the extraction process. As soon as the desired quantity of mixed bone cement is situated in the extraction syringe, said extraction syringe is detached from the extraction hollow cone.

The mixed bone cement preferably involves hydroxyl apatite in powder form, mixed with a bonding agent. Emerging after curing is a calcium phosphate salt of a high degree of hardness. An acrylic paste also can be produced.

Therapeutically, the mixed bone cement preferably is employed within the scope of kyphoplasty or vertebroplasty for injection in vertebra to be treated.

In general, the invention can be employed within the scope of therapeutic methods not requiring a large quantity of mixed bone cement. Consequently, cement can be mixed with the invention and transferred in application systems.

The invention also can be commercially distributed in such a way that the mixing beaker (1) already contains one of the two components of the bone cement, preferably the solid, ex factory. Then, after being filled with one component of the bone cement to be mixed, the mixing beaker (1) is sealed in a sterile manner by means of a cover film (5) affixed to a flange (4), and delivered in this way.

In this embodiment, the mixing beaker (1) is offered commercially in a sterile "set", together with cover (2) and manual stirring rod (6).

The invention claimed is:

1. A device for mixing bone cement comprising:
   a mixing beaker (1) that is open at an upper end; and
   a cover (2) to close the upper end;
   wherein the mixing beaker (1) has a concave beaker bottom (12) and raised side walls (11) with a corner-less cross section, without being circular;
   wherein the cover (2) features a shape with a cover bottom (22) that fits in the beaker bottom (12) with a perfect fit; and
   wherein provided at the lowermost point of the cover (2) is an extraction hollow cone (3), the interior of which pierces the cover bottom wall (22) and is designed for anchorage of an extraction syringe during removal by suction of the mixed bone cement.

2. The device according to claim 1, wherein the cross section of the raised side wall (11) of the mixing beaker (1) forms an approximate ellipse.

3. The device according to claim 1, wherein the beaker bottom (12) features a symmetrical axis (13), and the concavity of the beaker bottom (12) appears to be circular in axial cross section.

4. The device according to claim 1, wherein the raised side wall (11) of the mixing beaker (1) features a symmetrical axis (13) and runs parallel to the axis.

5. The device according to claim 1, wherein the angle of the opening of the extraction hollow cone (3) features a 6% incline of the side wall of said cone.

6. The device according to claim 1, wherein, provided on the raised side wall (11) of the mixing beaker (1) is a flange (4) in order to affix a cover film (5).

7. The device according to claim 2, wherein the interior space of the mixing beaker (1) features a width in the range of 44 to 49 mm±50% and a height in the range of 42 mm±50%.

8. Method for mixing bone cement with a device according to claim 1, comprising:
 a) mixing bone cement in a mixing beaker (1) by means of a manual stirring rod (6);
 b) inserting the cover (2) and displacing air above the mixed bone cement in the mixing beaker (1), with the center of the cover (2) featuring an extraction hollow cone (3), by which means bone cement mixed in the mixing beaker (1) can be extracted;
 c) introducing a port of an extraction syringe in the extraction hollow cone (3);
 d) extracting by suction the mixed bone cement by means of the extraction syringe from the mixing beaker (1) without a twisting of same, with the cover (2) lowering according to the extracted quantity of mixed bone cement; and
 e) detaching the extraction syringe from the extraction hollow cone (3).

9. Method according to claim 8, characterized in that polymethylmethacrylate is used as the mixed bone cement.

10. Method according to claim 8, characterized in that calcium phosphates or calcium sulphates are used as the mixed bone cement.

11. Method according to claim 8, characterized in that the mixed bone cement is employed for vertebroplasty.

12. Method according to claim 8, characterized in that the mixed bone cement is employed for kyphoplasty.

13. Method according to claim 8 further comprising providing a flange (4) on the raised side wall (11) of the mixing beaker (1), characterized in that the bone cement is mixed from two components, and one of said two components is provided in the mixing beaker (1), which is closed by means of a cover film (5) affixed to the flange (4).

* * * * *